US00PP35223P2

(12) United States Plant Patent
Nebelmeir

(10) Patent No.: US PP35,223 P2
(45) Date of Patent: Jun. 13, 2023

(54) ***OSTEOSPERMUM* PLANT NAMED 'LAZOST1831'**

(50) Latin Name: ***Osteospermum* L. X *Dimorphotheca* Moench**
Varietal Denomination: LAZOST1831

(71) Applicant: LAZZERI GENETICA S.A.S. di DALLAGO FRANCO & C., Merano (IT)

(72) Inventor: Johannes Nebelmeir, Hann. Munden (DE)

(73) Assignee: LAZZERI GENETICA S.A.S. di DALLAGO FRANCO & C., Merano (IT)

( * ) Notice: Subject to any disclaimer, the term of this patent is extended or adjusted under 35 U.S.C. 154(b) by 12 days.

(21) Appl. No.: 17/966,871

(22) Filed: Oct. 16, 2022

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Osteospermum* plant named 'LAZOST1831', characterized by its uniform and mounding plant habit; moderately vigorous growth habit; freely and uniformly branching habit; freely and early flowering habit; large single-type inflorescences with red purple and darker red purple bi-colored ray florets; and good garden performance.

1 Drawing Sheet

Figure 1:
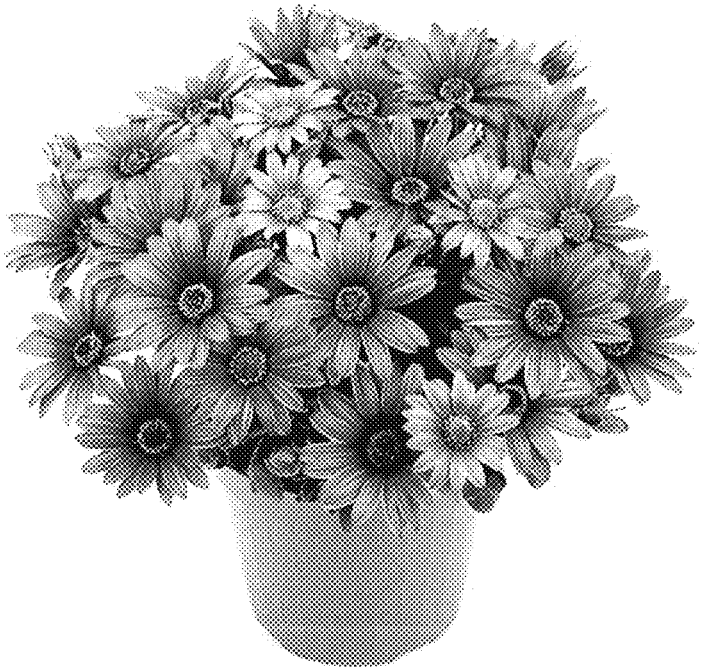

Botanical designation: *Osteospermum* L. X *Dimorphotheca* Moench.

Cultivar denomination: 'LAZOST1831'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Lazzeri Genetica S.A.S. di Dallago Franco & C. of Merano, Italy on Oct. 12, 2022, application number 2022/2194. Foreign priority is not claimed to this application.

BACKGROUND OF THE INVENTION

The present invention relates to a new and distinct cultivar of *Osteospermum* plant, botanically known as *Osteospermum* L. X *Dimorphotheca* Moench, and hereinafter referred to by the name 'LAZOST1831'.

The new *Osteospermum* plant is a product of a planned breeding program conducted by the Inventor in Merano, Italy. The objective of the program is to create and develop new interspecfic *Osteospermum* plants that are freely and uniformly branching with numerous large inflorescences with unique and attractive ray and disc floret coloration.

The new *Osteospermum* plant originated from an open-pollination during the summer of 2016 of a proprietary selection of *Osteospermum* L. X *Dimorphotheca* Moench identified as code number 13/132-3, not patented, as the female, or seed, parent with an unknown selection of *Osteospermum* L. X *Dimorphotheca* Moench as the male, or pollen, parent. The new *Osteospermum* plant was discovered and selected by the Inventor as a single flowering plant within the progeny of the stated open-pollination in a controlled greenhouse environment in Merano, Italy in the summer of 2017.

Asexual reproduction of the new *Osteospermum* plant by terminal vegetative cuttings in a controlled greenhouse environment in Merano, Italy since October, 2017 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LAZOST1831'. These characteristics in combination distinguish 'LAZOST1831' as a new and distinct *Osteospermum* plant:

1. Uniform and mounding plant habit.
2. Moderately vigorous growth habit.
3. Freely and uniformly branching habit.
4. Freely and early flowering habit.
5. Large single-type inflorescences with red purple and darker red purple bi-colored ray florets.
6. Good garden performance.

Plants of the new *Osteospermum* differ primarily from plants of the female parent selection in inflorescence size as plants of the new *Osteospermum* have larger inflorescence than plants of the female parent selection.

Plants of the new *Osteospermum* can be compared to plants of the *Osteospermum ecklonis* 'SummerSmile Magenta', not patented. In side-by-side comparisons, plants of the new *Osteospermum* differ primarily from plants of 'SummerSmile Magenta' in the following characteristics:

1. Plants of the new *Osteospermum* are more freely branching than plants of 'SummerSmile Magenta'.
2. Plants of the new *Osteospermum* have larger inflorescences than plants of 'SummerSmile Magenta'.
3. Ray florets of plants of the new *Osteospermum* are red purple and darker red purple bi-colored whereas ray florets of plants of 'SummerSmile Magenta' are purple and white bi-colored.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph at the top of the sheet (FIG. 1) is a side perspective view of a typical flowering plant of 'LAZOST1831' grown in a container.

Figure 2:
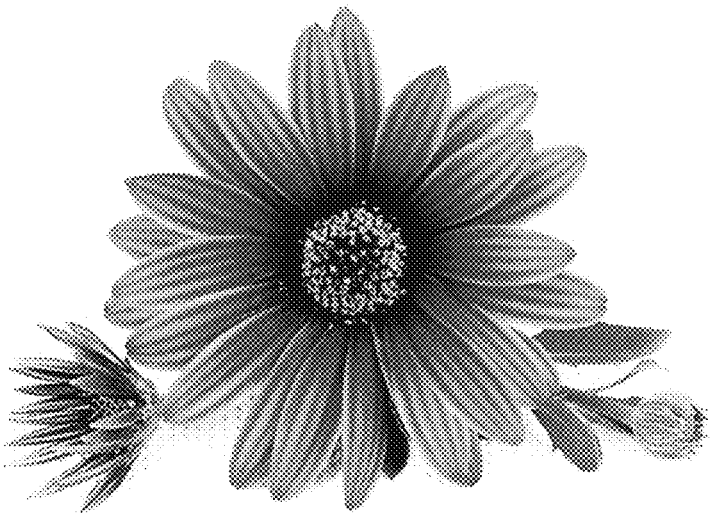

The photograph at the bottom of the sheet (FIG. 2) is a close-up view of a typical opening inflorescence, open inflorescence, leaves and an inflorescence bud of 'LAZOST1831'.

DETAILED BOTANICAL DESCRIPTION

The aforementioned photographs, following observations and measurements describe plants grown during the summer in 14-cm containers in a glass-covered greenhouse in Merano, Italy and under cultural practices typical of commercial *Osteospermum* production. During the production of the plants, day temperatures ranged from 18° C. to 22° C., night temperatures ranged from 12° C. to 18° C. and light levels averaged 3,000 lux. Plants were pinched one time and plants were 16 weeks old when the photographs and description were taken. In the following description, color references are made to The Royal Horticultural Society Colour Chart, 1995 Edition, except where general terms of ordinary dictionary significance are used.

Botanical classification: *Osteospermum* L. X *Dimorphotheca* Moench 'LAZOST1831'.

Parentage:

*Female, or seed, parent*.—Proprietary selection of *Osteospermum* L. X *Dimorphotheca* Moench identified as code number 13/132-3, not patented.

*Male, or pollen, parent*.—Unknown selection of *Osteospermum* L. X *Dimorphotheca* Moench, not patented.

Propagation:

*Type*.—Terminal vegetative cuttings.

*Time to initiate roots, summer*.—About seven days at temperatures about 22° C. to 25° C.

*Time to initiate roots, winter*.—About ten days at temperatures about 20° C. to 22° C.

*Time to produce a rooted cutting, summer*.—About 21 days at temperatures about 22° C. to 25° C.

*Time to produce a rooted cutting, winter*.—About 25 days at temperatures about 20° C. to 22° C.

*Root description*.—Medium in thickness, fibrous; typically greyish brown in color, actual color of the roots is dependent on substrate composition, water quality, fertilizers, substrate temperature and age of roots.

*Rooting habit*.—Moderately freely branching; medium density to dense.

Plant description:

*Plant form and growth habit*.—Uniform and mounding plant habit; freely branching habit, dense and bushy growth habit; moderately vigorous growth habit and moderate growth rate.

*Plant height, soil level to top of foliar plane*.—About 30 cm.

*Plant height, soil level to top of floral plane*.—About 35 cm.

*Plant diameter*.—About 25 cm.

*Lateral branches*.—Quantity per plant: Freely branching habit, about 12 to 14 primary lateral branches each with about three to four secondary lateral branches developing per plant; pinching enhances lateral branch development. Length: About 18 cm to 20 cm. Diameter: About 5 mm. Internode length: About 1 cm to 1.5 cm. Strength: Strong, sturdy. Aspect: About 45° from vertical. Texture and luster: Smooth, glabrous; semi-glossy. Color, developing and developed: Close to 143C.

*Leaf description*.—Arrangement: Alternate, simple. Length: About 5 cm to 6 cm. Width: About 3 cm. Shape: Elliptic. Apex: Acute to obtuse. Base: Attenuate. Margin: Slightly lobed with shallow and divergent sinuses. Texture and luster, upper surface: Smooth, glabrous; rugose; semi-glossy. Texture and luster, lower surface: Smooth, glabrous; rugose; matte. Venation pattern: Pinnate. Color: Developing leaves, upper surface: Close to 144A. Developing leaves, lower surface: Close to 143C. Fully expanded leaves, upper surface: Close to 137B; venation, close to 143B. Fully expanded leaves, lower surface: Close to 137D; venation, close to 143C. Petioles: Length: About 1.5 cm. Diameter: About 5 mm. Strength: Moderately strong. Texture and luster, upper and lower surfaces: Smooth, glabrous; semi-glossy. Color, upper and lower surfaces: Close to 143C.

Inflorescence description:

*Appearance and aspect*.—Terminal and axillary inflorescences; inflorescences positioned beyond the foliar plane on strong peduncles and face mostly upright to slightly outwardly; single-type inflorescence form with lanceolate-shaped ray florets and tubular disc florets; ray and disc florets developing acropetally on a capitulum.

*Flowering habit*.—Freely flowering habit; about 28 to 32 developing and open inflorescences per plant.

*Fragrance*.—None detected.

*Flowering response*.—Early flowering habit; in Italy, plants of the new *Osteospermum* begin flowering in March/April and flower continuously until first frost in the autumn; inflorescences persistent.

*Inflorescence buds*.—Height: About 1.5 cm. Diameter: About 1 cm. Shape: Ovoid. Texture and luster: Smooth, glabrous; rugose; matte. Color: Close to 138A.

*Inflorescence size*.—Diameter: About 6 cm to 8 cm. Depth (height): About 1.5 cm. Disc diameter: About 1 cm. Receptacle diameter: About 1.5 cm. Receptacle height: About 1 cm. Receptacle color: Close to 143C.

*Ray florets*.—Quantity per inflorescence and arrangement: About 20 to 22 arranged in one to two whorls. Length: About 3 cm. Width: About 1 cm. Shape: Roughly lanceolate. Apex: Acute to obtuse. Base: Cuneate. Margin: Entire; not undulate. Aspect: Mostly flat. Texture and luster, upper and lower surfaces: Smooth, glabrous; slightly glossy. Color: When opening and fully opened, upper surface: Close to 78B; venation, close to 81B; color does not change with subsequent development. When opening and fully opened, lower surface: Close to 81A; venation, close to 79A; color does not change with subsequent development.

*Disc florets*.—Quantity per inflorescence and arrangement: About 30 to 35 arranged in numerous whorls. Length: About 1.5 cm. Diameter: About 1.5 mm. Shape: Tubular with five pointed apices. Apex: Dentate. Aspect: Upright. Texture and luster: Smooth, glabrous; slightly glossy to matte. Color, inner and outer surfaces: Close to 79A.

*Phyllaries*.—Quantity per inflorescence and arrangement: About 14 to 16 arranged in a single whorl. Length: About 8 mm to 10 mm. Width: About 1 mm. Shape: Lanceolate. Apex: Acute. Base: Cuneate. Margin: Entire. Texture and luster, upper and lower surfaces: Smooth, glabrous; rugose; matte. Color, upper and lower surfaces: Close to 138A.

*Peduncles*.—Length: About 3 cm. Diameter: About 4 mm. Strength: Strong. Aspect: Upright to outwardly slanting. Texture and luster: Smooth, glabrous; matte. Color: Close to 138A.

*Reproductive organs*.—Androecium: Present on disc florets only. Filament length: About 3 mm. Filament color: Close to 156A. Anther size: About 3 mm by 1 mm. Anther shape: Oval. Anther color: Close to 93A. Pollen amount: Abundant. Pollen color: Close to 17A. Gynoecium: Present on ray florets only. Pistil length: About 3 mm. Stigma shape: Bi-parted. Stigma diameter: About 1 mm. Stigma color: Close to 93A. Style length: About 1 mm. Style color: Close to 156A. Ovary color: Close to 156A.

*Fruits and seeds*.—To date, fruit and seed development has not been observed on plants of the new *Osteospermum*.

Pathogen & pest resistance: Plants of the new *Osteospermum* have not been observed to be resistant to pathogens and pests common to *Osteospermum* plants.

Garden performance: Plants of the new *Osteospermum* have been observed to have good garden performance and to tolerate rain, wind and temperatures ranging from about 8° C. to about 35° C.

It is claimed:

1. A new and distinct *Osteospermum* plant named 'LAZOST1831' as illustrated and described.

* * * * *